US011116807B2

(12) United States Patent
Chen et al.

(10) Patent No.: US 11,116,807 B2
(45) Date of Patent: Sep. 14, 2021

(54) **ACTIVE SUBSTANCE OF *MORCHELLA*, ITS USE AND A COMPOSITION THEREOF FOR IMPROVING THE REPRODUCTIVE FUNCTION**

(71) Applicant: GRAPE KING BIO LTD., Taoyuan (TW)

(72) Inventors: Chin-Chu Chen, Taoyuan (TW); Szu-Yin Wu, Taoyuan (TW); Hsiao-Ling Chang, Taoyuan (TW); Yen-Po Chen, Taoyuan (TW)

(73) Assignee: GRAPE KING BIO LTD., Taoyuan (TW)

( * ) Notice: Subject to any disclaimer, the term of this patent is extended or adjusted under 35 U.S.C. 154(b) by 38 days.

(21) Appl. No.: 16/019,722

(22) Filed: Jun. 27, 2018

(65) Prior Publication Data
US 2019/0175673 A1    Jun. 13, 2019

(30) Foreign Application Priority Data

Dec. 13, 2017  (TW) ................................. 106143634

(51) Int. Cl.
| A61K 36/062 | (2006.01) |
| A61P 15/08 | (2006.01) |
| A61K 9/19 | (2006.01) |
| A61K 47/10 | (2017.01) |
| A61K 9/08 | (2006.01) |

(52) U.S. Cl.
CPC .............. *A61K 36/062* (2013.01); *A61K 9/08* (2013.01); *A61K 9/19* (2013.01); *A61K 47/10* (2013.01); *A61P 15/08* (2018.01)

(58) Field of Classification Search
CPC .......... A61K 36/062; A61K 9/08; A61K 9/19; A61K 47/10; A61P 15/08
See application file for complete search history.

(56) References Cited

U.S. PATENT DOCUMENTS

| 6,090,615 A  *  7/2000 | Nagaoka ................... C12N 1/06 |
| | 435/267 |
| 2016/0058049 A1*  3/2016 | Langan ................... A23L 29/30 |
| | 435/256.8 |

FOREIGN PATENT DOCUMENTS

| CN | 103141302 A | * | 6/2013 | |
| CN | 105154342 A | * | 12/2015 | |
| CN | 106190862 | * | 12/2016 | ............... C12N 1/14 |

(Continued)

OTHER PUBLICATIONS

Adamopoulos et. al., "Raised Sodium, Potassium, and Urea Concentrations in Spermatic Venous Blood: An Additional Causative Factor in the Testicular Dysfunction of Varicocele?" Fertility and Sterility, vol. 48, No. 2, Aug. 1987, pp. 331-333.

(Continued)

*Primary Examiner* — Jana A Hines
(74) *Attorney, Agent, or Firm* — Birch, Stewart, Kolasch & Birch, LLP

(57) ABSTRACT

The present invention provides an active substance of *Morchella*, its use and a composition thereof for improving disturbance of reproductive function, especially, for manufacturing a pharmaceutical composition to improve disturbance of reproductive function induced by obesity or metabolic syndrome. The composition with the active substance of *Morchella* can effectively improve the structural integrity of testicular tissues and sperm, increase testosterone levels in the blood, and reduce the oxidation stress in sperms.

8 Claims, 3 Drawing Sheets

C

D

D +ME

D+MC

(56) References Cited

FOREIGN PATENT DOCUMENTS

| CN | 106604650 A | * | 4/2017 | ............... | A23L 5/00 |
| WO | WO-2017056059 A1 | * | 4/2017 | ............. | A01G 18/00 |

OTHER PUBLICATIONS

Amaral et. al., "Diabetes and the Impairment of Reproductive Function: Possible Role of Mitochondria and Reactive Oxygen Species," Current Diabetes Reviews, vol. 4, No. 1, 2008, pp. 46-54 (10 pages total).

Corona et. al., "Type 2 Diabetes Mellitus and Testosterone: A Meta-analysis Study," International Journal of Andrology, vol. 34, ISSN 0105-6263, 2010, pp. 528-540.

Jelodar et. al., "Endocrine Profile and Testicular Histomorphometry in Adult Rat Offspring of Diabetic Mothers," J Physiol Sci, vol. 59, 2009 (Published online Jun. 18, 2009), pp. 377-382.

Kotaja et. al., "Abnormal Sperm in Mice with Targeted Deletion of the Act (Activator of cAMP-responsive Element Modulator in Testis) Gene," PNAS, vol. 101, No. 29, Jul. 20, 2004, pp. 10620-10625.

Parlaktas et. al., "Levels of Oxidative Stress Parameters and the Protective Effects of Melatonin in Psychosis Model Rat Testis," Asian J Androl, vol. 10, No. 2, 2008, pp. 259-265.

Sud et. al., "A Review of Toxic Effects and Aphrodisiac Action of *Morchella esculenta* (Wild Morel-Guchhi Mushroom)—A Himalayan Delight," European Journal of Pharmaceutical and Medical Research, vol. 4, No. 8, 2017, pp. 726-730.

Walker, "Testosterone Signaling and the Regulation of Spermatogenesis," Landes Bioscience, vol. 1, Issue 2, 2011, pp. 116-120.

Xiao, "Effect of Different Agitation Strategy on the Mycelia Growth of Morchella esculenta," Graduate Institute of Chemical Engineering, Tunghai University, Master Thesis, Jul. 2006, pp. 1-111 (115 pages total).

* cited by examiner

C

D

D +ME

D+MC

C

D

D +ME

D +MC

ACTIVE SUBSTANCE OF *MORCHELLA*, ITS USE AND A COMPOSITION THEREOF FOR IMPROVING THE REPRODUCTIVE FUNCTION

BACKGROUND OF THE INVENTION

Field of the Invention

The present invention relates to an active substance of *Morchella* for improving reproductive function, its use and composition thereof; more specifically, to a composition of *Morchella* for increasing testosterone levels, reducing the proportion of abnormal sperm, reducing oxidative stress in sperms, and improving structural integrity of testicular tissue induced by obesity or metabolic syndrome.

Description of the Prior Art

A reproductive function can be evaluated from different aspects, such as, but not limited to, the structural integrity of the testicular tissue, the number of abnormal sperms, the concentration of testosterone in the blood, or the oxidative stress in sperms.

Testis

A testis consists of several seminiferous tubules, which are supported by sertoli cells and separated by groups of Leydig cells. Spermatogenesis is regulated by sertoli cells and Leydig cells, and the concentration of androgens is also maintained by these cells to improve sperm maturation (Kotaja et al., 2004). From the aspect of tissue structure, immature sperm cells are located in the basal membrane of the seminiferous tubules and move to the luminal center of the seminiferous tubules as the sperms mature.

Testosterone

Testosterone is a steroid hormone derived from cholesterol, which is secreted mainly by a testis of a male or an ovary of a female. Statistics show that testosterone secretion of an adult male is about 20 times of that of an adult female, and the content of testosterone in an adult male is 7-8 times of that of an adult female.

Testosterone is the main male hormone in human bodies. Although testosterone tends to produce noticeable symptoms in males than females, it is equally important to women. Therefore, for both of men and women, testosterone has a significant impact on physical activities in human bodies. The benefits of testosterone include increasing libido, strength, stimulating the immune system, and preventing osteoporosis. Since testosterone can improve physical strength, some athletes have ingested testosterone before games to stimulate and optimize their conditions. However, at present, testosterone is banned in most sports.

After the age of 40, the concentration of circulating testosterone falls every year and would lead to a diagnosis of testosterone deficiency syndrome. This symptom is common in middle-aged and elderly men and is generally considered to be related to menopause. Although male menopause does not occur at a pronounced time as female menopause, symptoms of male menopause gradually become severe as the concentration of testosterone decreases. Common symptoms of male menopause include loss of libido, erectile dysfunction, diminished vitality, restlessness, depression, loss of enjoyment of life, decreased concentration, decreased work efficiency, and sleep disorders. In addition, the symptoms are accompanied by degeneration of secondary sexual characteristics, osteoporosis, increased fat, testicles shrinking, and gynecomastia. In addition to the above-mentioned symptoms, which affect the quality of life, many studies have found that the risks of osteoporosis, fractures, and cardiovascular diseases increase when there is not enough testosterone in a human body. Moreover, when serum testosterone levels in men are down, so is the concentration of sperm and/or the total number of sperms in semen, decreasing the probability of conception.

Another factor that influences testosterone levels is obesity. Previous studies have found that the total testosterone concentrations are lower in obese patients than in men with normal BMI, suggesting an inverse correlation between testosterone levels and BMI. Besides, almost one in every four obese people has a significantly lower concentration of testosterone in the blood. The mechanism underlying for this effect is that the aromatase enzyme in adipocytes catalyzes the conversion of testosterone to estrogen. Therefore, it is believed that a higher concentration of estrogen and a lower concentration of testosterone are in the blood of obese men due to the increase in available aromatase enzyme in the fatty tissue. In addition, the above-mentioned enhanced catalysis becomes more pronounced with age. However, research has also shown that obese individuals can restore normal testosterone levels through weight loss and exercise.

The concentration of testosterone in the blood of patients with metabolic syndrome is also relatively low compared to healthy males. Corona G et al. published a study on diabetes in people with metabolic syndrome (Type 2 diabetes mellitus and testosterone: a meta-analysis study) in 2010. This study demonstrated that there is a lower concentration of testosterone in the blood of type 2 diabetic patients, and points out that erectile dysfunction in patients with type 2 diabetes become worse when the concentration of testosterone decreases. Furthermore, Adamopoulos et al. (1987) and Jelodar et al. (2009) reported that diabetes mellitus can cause insulin resistance and inflammation, thereby inhibiting the release of hormone from the pituitary gland and production of testosterone from the Leydig cells in seminiferous tubules.

Oxidative Stress

Growing evidence indicates that oxidative stress is increased in diabetes and has deleterious effects on male reproductive function (Amaral et al., 2008). Oxidative stress can induce DNA fragmentation during sperm transportation or storage through the epididymis. Compared with other tissues, sperms contain more unsaturated fatty acids and therefore are more susceptible to ROS attack, resulting in sperm DNA fragmentation (Parlaktas et al., 2008).

*Morchella*

*Morchella* is a world-famous large edible fungus, belonging to *Ascomycetes, Pezizales, Morchellaceae, Morchella*. *Morchella* is named for its irregular folds, which looks like goat tripe in the upper part of its fruiting bodies. *Morchella* is also known as goat tripe mushroom, goat tripe vegetables, clogs bacteria, morel, etc. Bunyard et al. published a study in 1994 and divided *Morchella* into at least two groups by RFLP analysis of the 28S RNA gene: (1) black *Morchella*, which includes *M. angusticeps, M. conica*, and *M. elata*, with darker brown color at the head and a regular grid-like pattern of folds; (2) yellow *Morchella*, which includes *M. deliciosa, M. esculenta*, and *M. crassipes*, with a pale yellow to brown color at the head and irregular folds.

*Morchella* is widely distributed over all continents, especially in the temperate regions of the northern hemisphere, except the north and south poles. Its growing season is in late spring or early summer. As *Morchella* can only be harvested once a year, the prices of *Morchella* remain high due to limited production. However, *Morchella* is popular because of its tasty flavor and its rich nutritional value, as shown by the earliest record of artificial cultivation of *Morchella* in the 1880s. Nevertheless, the technology of artificial cultivation of fruiting bodies of *Morchella* has not yet been fully mastered. Although there has been semi-commercialized production in China, it is still limited due to many conditions. Therefore, the fermentation technology of *Morchella* mycelia emerged. The advantages of *Morchella* growing using liquid fermentation is that the fermentation parameters can be controlled, which lead to rapid growth of the mycelia, and thereby reduce the risk of contamination as the growth period is short. In addition, *Morchella* mycelia are tastier than its fruiting bodies, which create fewer barriers in product development.

*Morchella* is also extremely attractive in terms of health care. *Morchella* has been used as an edible mushroom since ancient times in China, and its records can be traced back to "Compendium of Materia Medica" of the Ming Dynasty. The article states that goat tripe vegetables (i.e. *Morchella*) is "cold and non-toxic, beneficial to the stomach, phlegm dispelling, and Qi regulating," which shows that *Morchella* has a certain physiological activity. In recent years, research has also proved the efficacy of *Morchella* by scientific methods, including anti-tumor, kidney protection, anti-fatigue, liver protection, anti-radiation, antibacterial, regulating immunity, and regulating gastrointestinal motility.

The present invention is the first study to demonstrate the effect of *Morchella* mycelia on sexual dysfunction induced by hyperglycemia, specifically, by administering the active substance of *Morchella* to increase the concentration of testosterone in blood, reduce the proportion of abnormal sperms, decrease oxidative stress of sperms, and/or improve type of testis tissue. The present invention provides another exploitable use of *Morchella* in the medical field, significantly enhancing the value of *Morchella* as a pharmaceutical composition.

SUMMARY OF THE INVENTION

The object of the present invention is to develop an active substance of *Morchella* for improving disturbance of reproductive function, prepared by the following methods:
(A) inoculating *Morchella* mycelia on a medium for solid-state culture;
(B) inoculating the *Morchella* mycelia cultured in step (a) in a liquid medium for liquid culture; and
(C) inoculating the *Morchella* mycelia cultured in step (b) in a fermenter for fermentation.

Preferably, the temperature of step (c) is 23 to 28° C., the ventilation is 0.5 to 1.0 vvm, the rotation speed is 30 to 50 rpm, and/or the number of cultivation day is 6 to 10 days.

Preferably, the *Morchella* is deposited in the Food Industry Research and Development Institute, with a deposit number BCRC-36352 and/or BCRC-36336.

Another object of the present invention is to develop a method for improving disturbance of reproductive function, comprising an effective amount of an active substance of *Morchella*.

Preferably, the *Morchella* comprises *Morchella esculenta*, *Morchella crassipes*, or a combination thereof.

Preferably, the active substance of *Morchella* is a lyophilized powder obtained after fermentation and freeze-drying of *Morchella* mycelia.

Preferably, the active substance of *Morchella* is an extract obtained by extracting *Morchella* mycelia with pure water or ethanol.

Preferably, the reproductive function comprises testosterone level, sperm type, oxidative stress in sperm, structural integrity of testicular tissues, or a combination thereof.

Preferably, improving the disturbance of reproductive function is increasing the testosterone levels in the blood.

Preferably, improving the disturbance of reproductive function is reducing the proportion of abnormal sperms with broken tails, bent tails, or bent necks.

Preferably, improving the disturbance of reproductive function is reducing the amount of ROS produced in sperms to reduce the oxidative stress in sperms.

Preferably, improving the disturbance of reproductive function is reducing the number and volume of gaps within the luminal center of seminiferous tubules or between the seminiferous tubules to improve the structural integrity of a testicular tissue.

Preferably, the disturbance of reproductive function is induced by obesity and/or metabolic syndrome.

Preferably, the metabolic syndrome is diabetes.

The present invention provides the benefits of *Morchella* in the medical field and further provides a composition for improving disturbance of reproductive function, which comprises an effective amount of an active substance of *Morchella*.

Preferably, the active substance of *Morchella* is a lyophilized powder obtained after fermentation and freeze-drying of *Morchella* mycelia.

Preferably, the active substance of *Morchella* is an extract obtained by extracting *Morchella* mycelia with pure water or ethanol.

Preferably, the effective amount is 500 mg/60 kg to 10 g/60 kg body weight/day.

Preferably, the composition further comprises an additive selected from the group consisting of an excipient, a preservative, a diluent, a filler, an absorption enhancer, a sweetener, and a combination thereof.

Preferably, the composition is a medicine, feed, drink, nutritional supplement, dairy product, food, or health food.

Preferably, the composition is in the form of powder, lozenge, granulation, microcapsule, ampoule, liquid spray, or suppository.

DETAILED DESCRIPTION OF THE EMBODIMENTS

Source of Fungus

Figure 1:
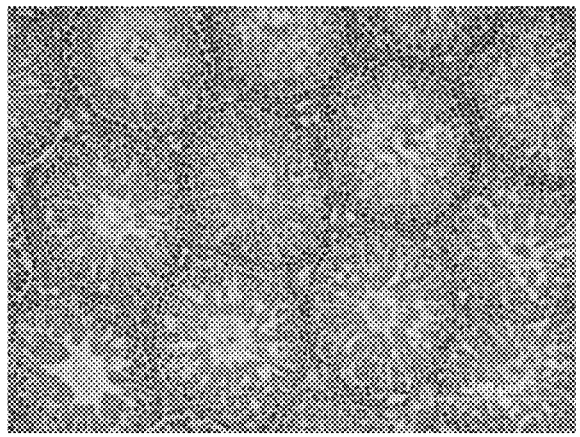
FIG. 1 shows the stained sections of testis tissues of the control group (C), the diabetic group (D), the diabetic group administered *Morchella esculenta* (D+ME), and the diabetic group administered *Morchella crassipes* (D+MC).
Figure 1:
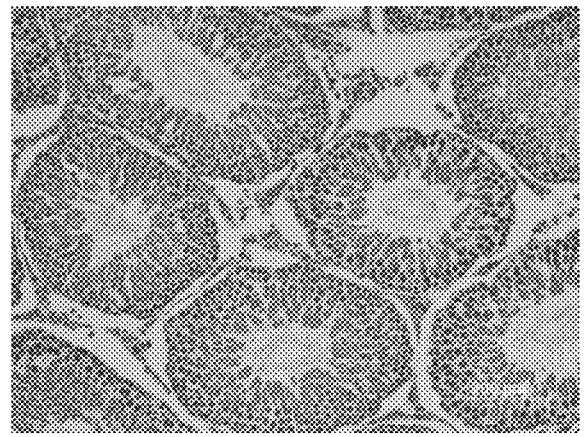
Figure 1:
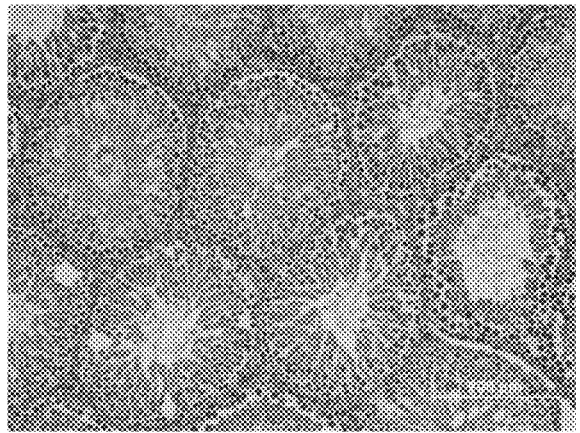
Figure 1:
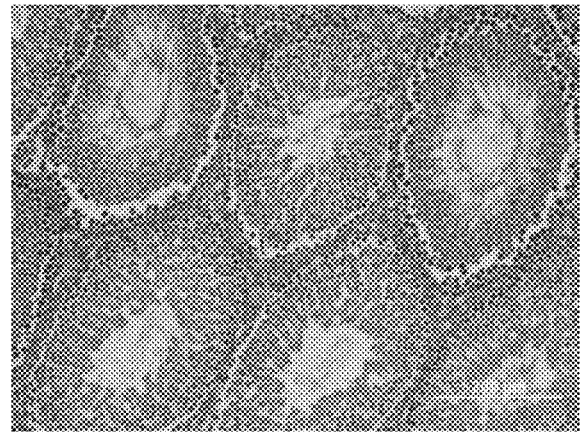

*Morchella* can be selected from the group consisting of *M. angusticeps, M. conica, M. elata, M. deliciosa, M. esculenta,* and *M. crassipes*. In a preferred embodiment, two *Morchella* species are purchased from the Bioresource Collection and Research Center (BCRC) of the Food Industry Research and Development Institute. One is *Morchella esculenta*, with a deposit number BCRC-36352, the other is *Morchella crassipes*, with a deposit number BCRC-36336. The active substances of *Morchella* of the present invention are not limited to the ones obtained by the above-mentioned species.

Fungus Cultivation

Mycelia of the purchased *Morchella* were inoculated on the solid medium to activate the fungus. In a preferred embodiment, the solid medium is Potato dextrose agar (PDA). After the growth of *Morchella* mycelia was complete, a cube of fresh mycelia together with the solid culture medium was inoculated into a flask containing 1 L of the liquid medium. In a preferred embodiment, the formulation of the liquid medium is shown in Table 1. In a preferred embodiment, the mycelia are liquid cultured under the conditions of a temperature of 25° C. and a speed of 50 to 150 rpm for 4 to 7 days to complete the growth of the mycelia.

TABLE 1

Formulation of the liquid medium is shown as follows:

| Composition | Proportion |
| --- | --- |
| Sucrose | 1-10% |
| Yeast extract, YE | 0.1-2% |
| Soybean powder | 1-10% |
| $KH_2PO_4$ | 0.01-0.2% |
| $MgSO_4$ | 0.01-0.2% |

Subsequently, the mycelia growing completely in the flask were inoculated in a sterilized medium in a 100-liter fermenter for mass production. In a preferred embodiment, the *Morchella* mycelia are mass-cultured at a temperature of 25° C., a ventilation of 0.5-1.0 vvm, and a rotational speed of 40 rpm for 6 to 10 days. When the dry weight of the mycelia stops increasing or when the sucrose residue was less than 1000 mg/L, the fermenter was heated to stop cultivation. In a preferred embodiment, the fermenter was heated to 100° C. for 15 minutes to stop cultivation.

Preparation of Lyophilized Powder

After fermentation was completed, a part of the whole fermented liquid (containing the culture medium and the mycelia) in the fermenter was spread on a plate and freeze-dried to prepare a "lyophilized powder of whole fermented liquid." In a preferred embodiment, the freeze-drying temperature is set at 30° C. and the freeze-drying duration is at least 3 days. The other part of the whole fermented liquid was centrifuged, and the *Morchella* mycelia were freeze-dried to obtain "lyophilized powder of mycelia." In a preferred embodiment, the whole fermented liquid was centrifuged at 4500 rpm by using a continuously centrifugal decanter centrifuge.

Preparation of Extract

An appropriate amount of "lyophilized powder of whole fermented liquid" was resuspended in pure water. In a preferred embodiment, the volume of pure water for resuspending is 5 to 40 times, more preferably 20 times, of the weight of the lyophilized powder. Subsequently, the mixture was heated at 121° C. for 20 minutes, and then the mycelia were removed by centrifugation (4500 rpm, using a continuously centrifugal decanter centrifuge) to obtain an extract of whole fermented liquid. The extract of whole fermented liquid was lyophilized to obtain "hot water extract." An appropriate amount of "lyophilized powder of mycelia" was resuspended with alcohol. In a preferred embodiment, the volume of the alcohol for resuspending is 5-40 times, more preferably 20 times, of the weight of the lyophilized powder. In a preferred embodiment, the concentration of alcohol is 95-100%. In a preferred embodiment, the alcohol is ethanol.

The resuspended lyophilized powder of mycelia was sonicated for 2 hours and then centrifuged (4500 rpm, using a continuously centrifugal decanter centrifuge) to obtain mycelium extraction. The mycelium extraction was concentrated under reduced pressure to obtain "ethanol extract." The hot water extract and the ethanol extract were thoroughly mixed to obtain an "extract mixture" as an active substance for *Morchella* feeding tests. In a preferred embodiment, the hot water extract and the ethanol extract are mixed in a ratio of 1:1 by weight.

Test Animals

Male 5-week old Sprague Dawley (SD) rats were purchased from BioLASCO Taiwan Co., Ltd. The transparent cages for the experimental rats were sterilized with 75% ethanol before the rats were put in. Two rats were housed in a cage at a temperature in the range of 23±1° C., with humidity maintained at 40-60%, light and dark cycles of 12/12 (7:00 a.m. to 6:59 p.m. bright, and 7:00 p.m. to 6:59 a.m. dark). Feed pellets (Laboratory Rodent Diet 5001, PMI® LabDiet®, St. Louis, Mo., U.S.A.), feed, and distilled water were supplied ad libitum.

Animal Feed

Feed powder Laboratory Rodent Diet 5001M (PMI Nutrition International, Inc., USA) was purchased from Young Li Co., and lard is selected as fat and was purchased from High Science Co., Ltd., (Taiwan). The formulation is shown as follows:

| Weight percentage (%) | Control Group | High-Fat Diet Group |
| --- | --- | --- |
| Crude protein | 23.9 | 21.5 |
| Crude fat | 5.0 | 18.4 |
| Carbohydrates | 53.8 | 40.8 |
| Ash | 7.0 | 6.0 |
| Others | 10.3 | 13.3 |

The feed of the high-fat diet group was made by adding lard to the feed powder, wherein the fat was 40% of total calories, to induce insulin resistance.

Test Groups

Male 5-week old Sprague-Dawley rats were housed for one week, with 8 in each group, for a total of 32 animals in four groups. One group was the control group while the other three groups were feed with the above animal feed and injected with streptozocin (STZ) to create diabetes model rats. Out of three diabetic groups, two groups were administrated with *Morchella esculenta* and *Morchella crassipes*, respectively.

Name and abbreviation of each group are shown as follows:

1. Control group (C)
2. Diabetes group HFD/STZ-Diabetes (D)
3. Diabetes group feeding *Morchella esculenta* (D+ME)
4. Diabetes group feeding *Morchella crassipes* (D+MC)

Tube Feeding and Sacrifice

After diabetes was successfully induced in the experimental rats, the rats were fed with samples by Tube Feeding. The extract mixture was dissolved in a carrier solution and fed with an amount of 500 mg/kg body weight (B.W.) to the

*Morchella esculenta* (D+ME) diabetic group and *Morchella crassipes* (D+MC) diabetic group. The control group was administered the same volume of vehicle solution (vehicle, 0.1 mol/L citric acid buffer, pH 4.5) as the volume administered to the experimental groups. Body weights of the experimental animals were measured and recorded weekly. After four weeks of sample feeding, the experimental animals underwent Oral Glucose Tolerance Test (OGTT). After animals of each group were fasted for 12 hours, blood was collected from tail vein, and concentration of blood glucose was measured. At the end of the experiment, carbon dioxide was used for anesthesia of the rats, syringe and centrifuge tube were pre-wetted with heparin (500 IU/mL), and blood was drawn from the abdominal aorta to sacrifice the rats. The obtained blood was taken as whole blood, loaded into a 15 mL centrifuge tube, and centrifuged at 3000×g for 15 minutes at 4° C. After centrifugation, the supernatant was collected as rat plasma. At the same time, the rats were sacrificed and the organs were removed and weighed. Liver, testis, and hypothalamus were stored at −80° C. for further experimental analyses, while sperms in epididymis were analyzed on the day of sacrifice.

Sections and Staining of Testis

Rats were sacrificed, and their testes were immersed in 10% formaldehyde (formalin) for later use. The testis tissues fixed with formaldehyde were cut with a scalpel to obtain a thickness of 0.5 cm tissue. Afterward, the tissues were immersed in formaldehyde again. Stained sections of the testis tissues were prepared by hematoxylin and eosin (H&E) staining. In hematoxylin and eosin (H&E) staining, hematoxylin is a basic dye for staining nucleus chromatin and cytoplasmic ribosomes a purplish blue, and eosin is an acid dye for staining the composition of the cytoplasm and extracellular matrix red. Therefore, based on the staining results, the structure of the tissues can be determined. After the sections of rat testis tissues were stained, the type of the seminiferous tubules of the testes was observed.

Collection of Sperms

Sperms in the epididymis were collected using a swim-up method. The epididymis was removed from the sacrificed rats and placed in a beaker containing 8 mL of RPMI culture medium. Epididymis was cut in two sections with dissecting scissors, placed on a rocker to shake for 10 minutes, and centrifuged at 190×g for 5 minutes. After centrifugation, the samples were placed in an incubator with 5% carbon dioxide at 37° C. for 30 minutes. Finally, sperms with better activity in the upper layer were collected to observe the abnormalities of the sperms.

Determination of Testosterone Levels

Concentrations of testosterone in the serum of the plasma samples were tested by testosterone ELISA kits. 50 μL of rat plasma were added to 50 μL of acetylcholinesterase (AChE) and anti-testosterone plasma for reaction. Next, the supernatant was removed and washed 5 times with a wash buffer. Ellman's reagent was added as AChE substrate and shaken in the dark for 80 minutes to complete the test sample. The absorbance of the sample at 412 nm was measured with an ELISA reader, and the concentration of testosterone (ng/mL) in the serum was obtained by converting the standard curve of the standard into the absorbance of the sample.

ROS Assay

DCFH-DA is a fluorescent probe that does not itself fluoresce. When DCFH-DA enters a cell, hydrolysis by esterase generates a non-fluorescent polar substance, DCFH, which is oxidized by intracellular ROS after it enters the cell, making it a fluorescent DCF, which can indirectly measure the amount of intracellular ROS production.

DCFH-DA was added to sperm RPMI solution containing $1 \times 10^6$ sperms/mL by adjusting the obtained 1 mL sperm of each group to a final concentration of 20 μM and incubated at 37° C. for 30 minutes. Then, the samples were centrifuged at 760×g for 5 minutes. The supernatant was removed after centrifugation and washed once with PBS. The samples were centrifuged again to remove supernatant, and 1 mL of PBS was added to resuspend the cells. The samples were analyzed by flow cytometry, which uses cell quest software. Ten thousand (10,000) cells were collected as a test sample, and the fluorescence intensity emitted by the machine was used to estimate the amount of ROS in the cells of the test samples. A high absorbance indicates a high level of ROS in the cells of the samples.

Statistical Analysis

Statistical analysis of the data was conducted using Statistical Product & Service Solutions (SPSS) software version 19.0, and the experimental results are expressed as Mean±S.E.M. Line charts were plotted using a Paired-Sample T-test with a statistical significance of $p<0.01$ (**) and $p<0.05$ (*). Histograms were plotted based on One-way analysis of variance One-way ANOVA and then using Duncan's Test for multiple comparison methods, with $p<0.05$ representing statistically significant differences.

Based on the experimental results obtained from the above experiments, the details are described as follows.

The Integrity of Testicular Tissues

Staining results of rat testis tissues are shown in FIG. 1. A significant number of enlarged lumen was observed within the seminiferous tubules of the diabetic group (D) as compared to the control group (C) of the non-induced diabetic group, indicating that the number of sertoli cells in the seminiferous tubules of the diabetic group (D) was significantly smaller than that of the control group (C). In addition, there are greater gaps between the seminiferous tubules of the diabetic group (D), indicating that the number of Leydig cells of the diabetic group (D) was also smaller than that of the control group (C). Based on the experimental results from the control group (C) and the diabetic group (D), suggesting that that diabetes induced by a high-fat diet can cause damage to the testicular tissues and can decrease a significant amount cells in the seminiferous tubules by enlarging lumen in and between the tissues.

In contrast, gaps within the luminal center of the seminiferous tubules or between the seminiferous tubules of the diabetes groups feeding *Morchella esculenta* (D+ME) and *Morchella crassipes* (D+MC) are significantly fewer when compared to the diabetic group (D), indicating that these groups have more sertoli cells and Leydig cells. Based on the results of the stained sections of the testicular tissues, the decreased number of sertoli cells and Leydig cells in the testis caused by diabetes can be restored back to normal status by administration of the active substance of *Morchella*, suggesting that *Morchella* has a beneficial effect on the male reproductive function.

Type of Sperms

Figure 2:
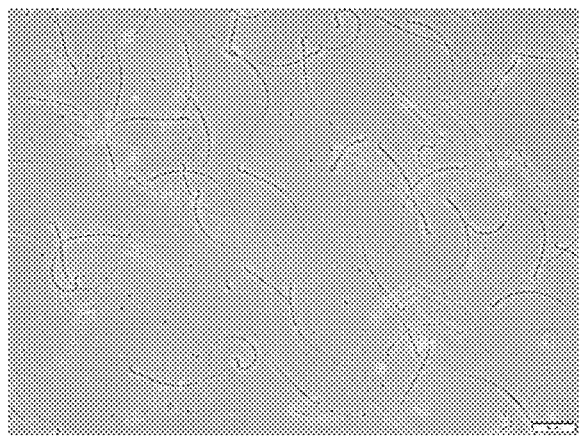
FIG. 2 shows the type of sperms of the control group (C), the diabetic group (D), the diabetic group administered *Morchella esculenta* (D+ME), and the diabetic group administered *Morchella crassipes* (D+MC).
Figure 2:
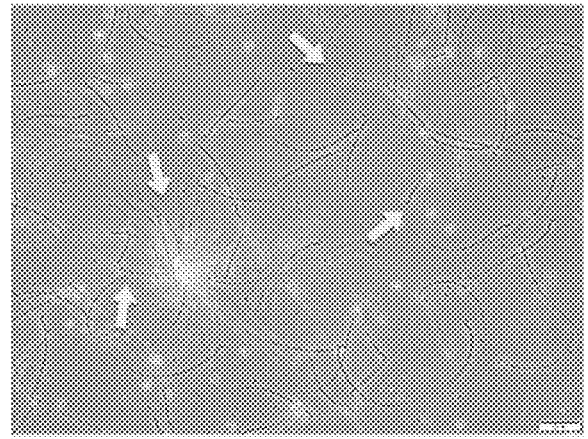
Figure 2:
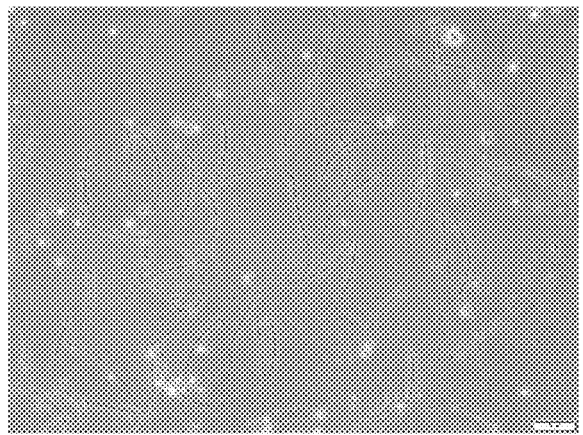
Figure 2:
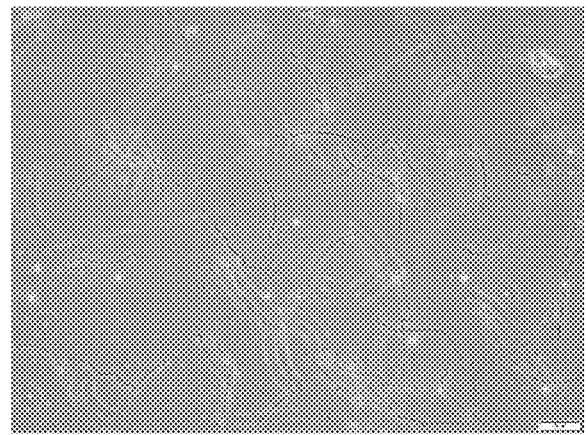

The collected sperms are shown in FIG. 2. Diabetic group (D) has a higher proportion of abnormal sperms than those in the control group (C). Examples of abnormal types include broken tails, bent tails, or bent necks of sperms. The two yellow arrows on the right on the photo of diabetic group (D) refer to sperms with bent necks, while the two yellow arrows on the left on the photo of diabetic group (D) refer to sperms with broken tails.

In contrast, sperm in diabetes groups feeding *Morchella esculenta* (D+ME) and *Morchella crassipes* (D+MC) have similar structures to those in the control group (C), indicating that administrating the active substances of *Morchella* can reduce structural damages on sperms caused by diabetes.

Testosterone Levels

Figure 3:
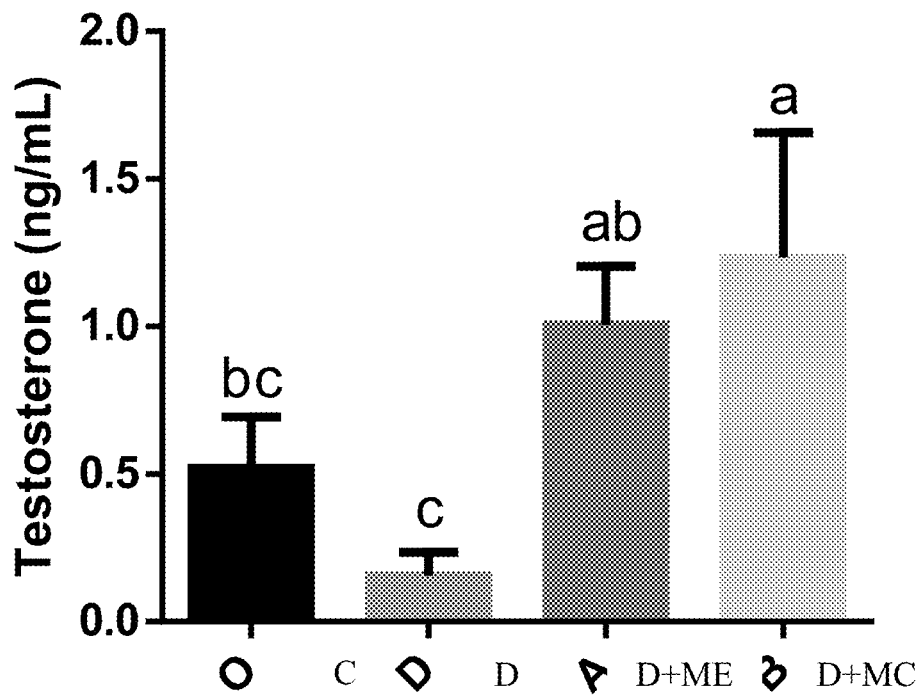
FIG. 3 shows the content of testosterone in plasma of the control group (C), the diabetic group (D), the diabetic group administered *Morchella esculenta* (D+ME), and the diabetic group administered *Morchella crassipes* (D+MC).

The results of the testosterone levels in rat plasma samples are shown in FIG. 3. The testosterone levels in the plasma of the diabetic group (D) is less than about 0.25 ng/mL, whereas that of the control group (C) of the non-induced diabetic group is about 0.5 ng/mL, indicating that the testosterone levels in the plasma of the diabetic group (D) are less than that of the control group (C).

In contrast, the testosterone levels of two diabetes groups feeding *Morchella esculenta* (D+ME) and *Morchella crassipes* (D+MC) is about 1.0 ng/mL and 1.25 ng/mL, respectively, which are both higher than that of the diabetic group (D). The testosterone levels in both D+ME and D+MC groups were significantly higher when compared to that of the control group (C). Based on these results, it is shown that administration of active substances of *Morchella* can stimulate increases in the low secretion or production of testosterone caused by diabetes.

ROS Content

Figure 4:
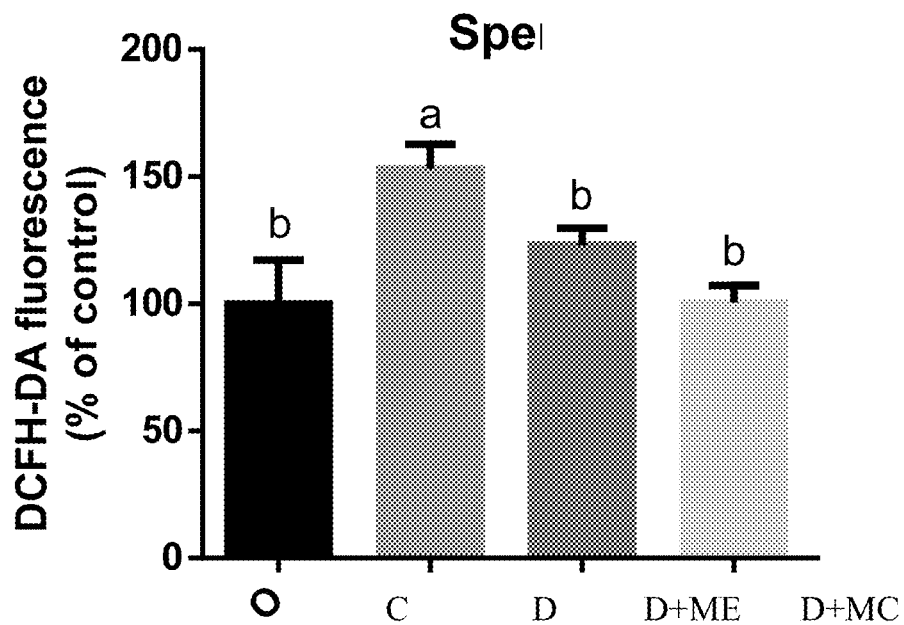
FIG. 4 shows the ROS content in sperms of the control group (C), the diabetic group (D), the diabetic group administered *Morchella esculenta* (D+ME), and the diabetic group administered *Morchella crassipes* (D+MC).

The results of ROS content in sperms are shown in FIG. 4. The fluorescence of the ROS generated by the control group (C) of the non-induced diabetic group is defined as 100%. The fluorescence of the ROS generated by the diabetic group (D) was significantly higher and about 150% of that of the control group (C), which is 1.5 times of the fluorescence of the control group.

In contrast, ROS content of diabetes groups feeding *Morchella esculenta* (D+ME) and *Morchella crassipes* (D+MC) decreased to about 120% and 100%, respectively, which are similar to the content of the control group (C). Based on these results, it can be concluded that administration of active substances of *Morchella* can reduce the oxidative stress caused by diabetes.

Based on the above experimental results, it was confirmed that the active substance extracted from *Morchella* can increase the reproductive function of male animals, suggesting a novel use of *Morchella* in the medical field is developed. Therefore, a composition comprising the active substance of *Morchella* can be manufactured and administered to an individual in an effective amount to achieve a healing effect in the reproductive function.

As used herein, an "effective amount" refers to an amount that is sufficient to produce the aforementioned prophylactic and/or therapeutic effect. Based on in vitro cell culture experiments, the aforementioned effective amount is defined as "µg/ml" based on the total volume of cell culture medium used in each culture. Based on animal model experiments, the aforementioned effective amount is defined as "g/60 kg body weight/day." In addition, the data of effective amount obtained via in vitro cell culture experiments can be converted to a reasonable effective amount for animal use by the following formula:

1. In general (Reagan-Shaw et al., 2008), 1 "µg/ml" units (based on the effective amount of in vitro cell culture experiments) may be equivalent to 1 "mg/kg body weight/day" units (based on the effective amount of rat model experiments), and, based on that metabolic rate of a rat is six times of that of a human, the effective human dose can be found.
2. Therefore, an effective amount for use in mice based on an in vitro cell culture experiment of 500 µg/ml is calculated as 500 mg/kg body weight/day (i.e., 0.5 g/kg body weight/day). Further, taking into account the differences in the aforementioned metabolic rates, an effective amount for human use may be taken as 5 g/60 kg body weight/day.
3. Based on the test results reported above, a validated dose based on a rat experiment is 500 mg/kg body weight/day and, therefore, a reasonably effective dose for human use should be 5 g/60 kg body weight/day.

In a preferred embodiment, an effective amount of the active substance of *Morchella* contained in the composition is 500 mg/60 kg to 10 g/60 kg body weight/day.

The composition further comprises an additive. In a preferred embodiment, the additive may be an excipient, a preservative, a diluent, a filler, an absorption enhancer, a sweetener, or a combination thereof. The excipient can be selected from sodium citrate, calcium carbonate, calcium phosphate, or a combination thereof. This preservative, such as benzyl alcohol, parabens, extends the shelf life of pharmaceutical compositions. The diluent can be selected from water, ethanol, propylene glycol, glycerol, or a combination thereof. The filler can be selected from lactose, nougat, ethylene glycol of high molecular weight, or a combination thereof. Absorption enhancers may be selected from dimethylsulfoxide (DMSO), laurocapram, propylene glycol, glycerol, polyethylene glycol, or a combination thereof. The sweetener may be selected from Acesulfame K, aspartame, saccharin, sucralose, neotame, or a combination thereof. In addition to the additives listed above, other additives that are suitable for use may be selected based on requirements without affecting the medical effect of the active substance of *Morchella*.

The composition can be developed as a different product in the medical field. In a preferred embodiment, the composition is a pharmaceutical product, feed, beverage, nutritional supplement, dairy product, food, or health food.

The composition may take different forms depending on the needs of the receiver. In a preferred embodiment, the composition is in the form of powder, lozenge, granulation, microcapsule, ampoule/ampule, liquid spray, or suppository.

The composition of the invention can be used in animals or humans. Without affecting the effect of the active substance of *Morchella*, the composition comprising the active substance of *Morchella* can be made into any pharmaceutical form and administered to the animal or human in a suitable manner depending on the type of the drug.

Preparation of the Composition

Composition 1: The hot water extract (20 wt %) was taken as the active substance of *Morchella*, mixed well with benzyl alcohol (8 wt %) as a preservative, glycerin (7 wt %) as a diluent, and dissolved in purified water (65 wt %) to produce a pharmaceutical composition of the present invention in liquid form. The aforementioned wt % means the ratio of each ingredient to the total weight of the composition. Store at 4° C. for later use.

Composition 2: The ethanol extract (15 wt %) was used as the active substance of *Morchella*, mixed well with benzyl alcohol (5 wt %) as preservative, glycerin (10 wt %) as a diluent, and dissolved in purified water (70 wt %) to produce a pharmaceutical composition of the present invention in liquid form. The aforementioned wt % means the ratio of each ingredient to the total weight of the composition. Store at 4° C. for later use.

What is claimed is:

1. An active substance of *Morchella* for improving disturbance of reproductive function, prepared by the following methods:
   (A) inoculating *Morchella* mycelia on a medium for solid-state culture;

(B) inoculating the *Morchella* mycelia cultured in step (a) in a liquid medium for liquid culture;

(C) inoculating the *Morchella* mycelia cultured in step (b) in a fermenter for fermentation to obtain whole fermented liquid containing the culture medium and the *Morchella* mycelia; and (D) extracting the whole fermented liquid with hot water or ethanol to obtain an extract;

wherein the *Morchella* comprises *Morchella esculenta*, which is deposited in the Food Industry Research and Development Institute with a deposit number BCRC-36352, *Morchella crassipes*, which is deposited in the Food Industry Research and Development Institute with a deposit number BCRC-36336, or a combination thereof.

2. The active substance of claim 1, wherein a temperature of step (c) is 23 to 28° C., the ventilation is 0.5 to 1.0 vvm, the rotation speed is 30 to 50 rpm, and/or the number of cultivation day is 6 to 10 days.

3. A composition for improving disturbance of reproductive function, comprising an effective amount of an active substance of *Morchella* of claim 1.

4. The composition of claim 3, wherein the active substance of *Morchella* is a lyophilized powder obtained after fermentation and freeze-drying of *Morchella* mycelia.

5. The composition of claim 3, wherein the active substance of *Morchella* is an extract obtained by extracting *Morchella* mycelia with hot water or ethanol.

6. The composition of claim 3, further comprising an additive selected from the group consisting of an excipient, a preservative, a diluent, a filler, an absorption enhancer, a sweetener, and a combination thereof.

7. The composition of claim 3, which is a medicine, feed, drink, nutritional supplement, dairy product, food, or health food.

8. The composition of claim 3, which is in the form of powder, lozenge, granulation, microcapsule, ampoule, liquid spray, or suppository.

* * * * *